(12) United States Patent
Swisher et al.

(10) Patent No.: US 7,828,773 B2
(45) Date of Patent: Nov. 9, 2010

(54) SAFETY RESET KEY AND NEEDLE ASSEMBLY

(75) Inventors: David R. Swisher, St. Charles, MO (US); Kimberly A. Moos, Florissant, MO (US)

(73) Assignee: Covidien AG (CH)

( * ) Notice: Subject to any disclaimer, the term of this patent is extended or adjusted under 35 U.S.C. 154(b) by 1519 days.

(21) Appl. No.: 11/179,090

(22) Filed: Jul. 11, 2005

(65) Prior Publication Data

US 2007/0016138 A1 Jan. 18, 2007

(51) Int. Cl.
*A61M 5/32* (2006.01)
(52) U.S. Cl. .................. 604/162; 604/110; 600/562; 600/567
(58) Field of Classification Search ............ 604/164.08, 604/162, 110, 192, 198; 600/562, 567
See application file for complete search history.

(56) References Cited

U.S. PATENT DOCUMENTS

| | | |
|---|---|---|
| 1,115,561 A | 11/1914 | Northey |
| 1,436,707 A | 11/1922 | Gaschke |
| 1,518,531 A | 12/1924 | Lung |
| 2,219,605 A | 6/1938 | Turkel |
| 2,854,976 A | 10/1958 | Heydrich |
| 3,254,533 A | 6/1966 | Tongret |
| 3,539,034 A | 11/1970 | Tafeen |
| 3,610,240 A | 10/1971 | Harautuneian |
| 3,681,991 A | 8/1972 | Eberly, Jr. |
| 3,729,998 A | 5/1973 | Mueller et al. |
| 3,822,598 A | 7/1974 | Brothers et al. |
| 3,884,230 A | 5/1975 | Wulff |
| 3,890,971 A | 6/1975 | Leeson et al. |
| 3,893,058 A | 7/1975 | Keith |
| 3,893,445 A | 7/1975 | Hofsess |
| 3,904,033 A | 9/1975 | Haerr |

(Continued)

FOREIGN PATENT DOCUMENTS

DE 3805567 A1 8/1989

(Continued)

OTHER PUBLICATIONS

Office action dated Jan. 11, 2010 from related U.S. Appl. No. 11/179,696, 8 pgs.

(Continued)

*Primary Examiner*—Nicholas D Lucchesi
*Assistant Examiner*—Laura A Bouchelle
(74) *Attorney, Agent, or Firm*—Lisa E. Winsor, Esq.

(57) ABSTRACT

A safety reset key is used to release a locking mechanism holding a safety shield in place over a sharp tip of a needle. In one embodiment, the reset key has ribs that are received in peripheral slots on the safety shield to engage an unlocking mechanism that unlocks a connection of the safety shield to the needle to allow the safety shield to be moved along the needle to expose the sharp tip, such as may be necessary for a second use of the needle. In another embodiment, the reset key includes a shroud that receives the shield to prevent the shield from being inadvertently pulled off of the needle when removing the key. The reset key may be associated with an obturator used to remove biological material from a central axial passageway of the needle.

20 Claims, 11 Drawing Sheets

U.S. PATENT DOCUMENTS

| | | |
|---|---|---|
| 3,915,003 A | 10/1975 | Adams |
| 3,946,613 A | 3/1976 | Silver |
| 3,976,070 A | 8/1976 | Dumont |
| 4,008,614 A | 2/1977 | Turner |
| 4,010,737 A | 3/1977 | Vilaghy et al. |
| 4,026,287 A | 5/1977 | Haller |
| 4,099,518 A | 7/1978 | Baylis et al. |
| D249,475 S | 9/1978 | Turner et al. |
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard |
| 4,643,199 A | 2/1987 | Jennings |
| 4,643,200 A | 2/1987 | Jennings |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters |
| 4,693,708 A | 9/1987 | Wanderer |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico |
| 4,810,248 A | 3/1989 | Masters |
| 4,813,426 A | 3/1989 | Haber et al. |
| 4,816,022 A | 3/1989 | Poncy |
| D300,728 S | 4/1989 | Ross |
| 4,819,659 A | 4/1989 | Sitar |
| 4,820,275 A | 4/1989 | Haber et al. |
| 4,826,488 A | 5/1989 | Nelson |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski |
| 4,986,279 A | 1/1991 | O'Neill |
| 4,994,041 A | 2/1991 | Dombrowski |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis |
| 5,108,374 A | 4/1992 | Lemieux |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,172,702 A | 12/1992 | Leigh et al. |
| 5,176,256 A | 1/1993 | Sawaya |

| | | | | | |
|---|---|---|---|---|---|
| 5,183,468 A | 2/1993 | McLees | 5,487,734 A | 1/1996 | Thorne et al. |
| 5,195,533 A | 3/1993 | Chin et al. | 5,492,532 A | 2/1996 | Ryan et al. |
| 5,195,985 A | 3/1993 | Hall | 5,501,675 A | 3/1996 | Erskine |
| 5,213,115 A | 5/1993 | Zytkovicz et al. | 5,507,296 A | 4/1996 | Bales et al. |
| 5,215,525 A | 6/1993 | Sturman | 5,507,297 A | 4/1996 | Slater et al. |
| 5,215,528 A | 6/1993 | Purdy et al. | 5,507,298 A | 4/1996 | Schramm et al. |
| 5,215,533 A | 6/1993 | Robb | 5,514,100 A | 5/1996 | Mahurkar |
| 5,217,438 A | 6/1993 | Davis | 5,514,152 A | 5/1996 | Smith |
| 5,228,451 A | 7/1993 | Bales et al. | 5,522,398 A | 6/1996 | Goldenberg et al. |
| 5,256,149 A | 10/1993 | Banik et al. | 5,526,821 A | 6/1996 | Jamshidi |
| 5,257,632 A | 11/1993 | Turkel et al. | 5,533,516 A | 7/1996 | Sahatjian |
| 5,279,306 A | 1/1994 | Mehl | 5,533,974 A | 7/1996 | Gaba |
| 5,279,563 A | 1/1994 | Brucker et al. | 5,538,009 A | 7/1996 | Byrne et al. |
| 5,279,591 A | 1/1994 | Simon | 5,542,927 A | 8/1996 | Thorne et al. |
| 5,282,477 A | 2/1994 | Bauer | 5,549,565 A | 8/1996 | Ryan et al. |
| 5,295,977 A | 3/1994 | Cohen et al. | 5,549,708 A | 8/1996 | Thorne et al. |
| 5,304,136 A | 4/1994 | Erskine | 5,553,624 A | 9/1996 | Francese et al. |
| 5,312,359 A | 5/1994 | Wallace | 5,558,651 A | 9/1996 | Crawford |
| 5,314,406 A | 5/1994 | Arias et al. | 5,562,629 A | 10/1996 | Haughton |
| 5,316,013 A | 5/1994 | Striebel, II et al. | 5,562,633 A | 10/1996 | Wozencroft |
| 5,320,635 A | 6/1994 | Smith | 5,562,683 A | 10/1996 | Chan |
| 5,322,517 A | 6/1994 | Sircom et al. | 5,569,217 A | 10/1996 | Luther |
| 5,324,288 A | 6/1994 | Billings et al. | 5,569,299 A | 10/1996 | Dill et al. |
| 5,328,482 A | 7/1994 | Sircom et al. | 5,570,783 A | 11/1996 | Thorne et al. |
| 5,331,971 A | 7/1994 | Bales et al. | 5,573,008 A | 11/1996 | Robinson et al. |
| 5,331,972 A | 7/1994 | Wadhwani et al. | 5,573,510 A | 11/1996 | Isaacson |
| 5,334,158 A | 8/1994 | McLees | 5,578,015 A | 11/1996 | Robb |
| 5,338,311 A | 8/1994 | Mahurkar | 5,584,809 A | 12/1996 | Gaba |
| 5,338,314 A | 8/1994 | Ryan | 5,584,810 A | 12/1996 | Brimhall |
| 5,341,816 A | 8/1994 | Allen | 5,584,818 A | 12/1996 | Morrison |
| 5,344,408 A | 9/1994 | Partika | 5,586,990 A | 12/1996 | Hahnen et al. |
| 5,348,022 A | 9/1994 | Leigh et al. | 5,591,202 A | 1/1997 | Slater et al. |
| 5,348,544 A | 9/1994 | Sweeney et al. | 5,595,186 A | 1/1997 | Rubinstein et al. |
| 5,356,421 A | 10/1994 | Castro | 5,599,310 A | 2/1997 | Bogert |
| 5,357,974 A | 10/1994 | Baldridge | 5,601,536 A | 2/1997 | Crawford et al. |
| 5,368,045 A | 11/1994 | Clement et al. | 5,601,585 A | 2/1997 | Banik et al. |
| 5,368,046 A | 11/1994 | Scarfone et al. | 5,601,599 A | 2/1997 | Nunez |
| 5,370,623 A | 12/1994 | Kreamer | 5,611,781 A | 3/1997 | Sircom et al. |
| D354,921 S | 1/1995 | Narayanan | 5,615,690 A | 4/1997 | Giurtino et al. |
| 5,385,151 A | 1/1995 | Scarfone et al. | 5,616,135 A | 4/1997 | Thorne et al. |
| 5,385,570 A | 1/1995 | Chin et al. | 5,623,969 A | 4/1997 | Raines |
| 5,389,104 A | 2/1995 | Hahnen et al. | 5,624,459 A | 4/1997 | Kortenbach et al. |
| 5,394,885 A | 3/1995 | Francese | 5,630,506 A | 5/1997 | Thorne et al. |
| 5,395,375 A | 3/1995 | Turkel et al. | 5,630,837 A | 5/1997 | Crowley |
| 5,396,900 A | 3/1995 | Slater et al. | 5,632,555 A | 5/1997 | Gregory |
| 5,399,167 A | 3/1995 | Deniega | 5,634,473 A | 6/1997 | Goldenberg et al. |
| 5,403,283 A | 4/1995 | Luther | 5,643,307 A | 7/1997 | Turkel et al. |
| 5,405,323 A | 4/1995 | Rogers et al. | 5,656,031 A | 8/1997 | Thorne et al. |
| 5,405,388 A | 4/1995 | Fox | 5,662,610 A | 9/1997 | Sircom |
| 5,409,461 A | 4/1995 | Steinman | 5,666,965 A | 9/1997 | Bales et al. |
| 5,411,486 A | 5/1995 | Zadini | 5,669,883 A | 9/1997 | Scarfone et al. |
| 5,415,182 A | 5/1995 | Chin et al. | 5,672,161 A | 9/1997 | Allen |
| 5,417,659 A | 5/1995 | Gaba | 5,679,907 A | 10/1997 | Ruck |
| 5,417,709 A | 5/1995 | Slater | 5,685,852 A | 11/1997 | Turkel et al. |
| 5,419,766 A | 5/1995 | Chang et al. | 5,685,862 A | 11/1997 | Mahurkar |
| 5,421,522 A | 6/1995 | Bowen | 5,687,907 A | 11/1997 | Holden |
| 5,423,766 A | 6/1995 | Di Cesare | 5,690,619 A | 11/1997 | Erskine |
| 5,425,718 A | 6/1995 | Tay | 5,693,022 A | 12/1997 | Haynes |
| 5,425,884 A | 6/1995 | Botz | 5,693,031 A | 12/1997 | Ryan et al. |
| 5,429,138 A | 7/1995 | Jamshidi | 5,695,467 A | 12/1997 | Miyata et al. |
| 5,429,616 A | 7/1995 | Schaffer | 5,695,521 A | 12/1997 | Anderhub |
| 5,454,378 A | 10/1995 | Palmer et al. | 5,697,904 A | 12/1997 | Raines et al. |
| 5,456,267 A | 10/1995 | Stark | 5,697,907 A | 12/1997 | Gaba |
| 5,458,658 A | 10/1995 | Sircom | 5,700,249 A | 12/1997 | Jenkins |
| 5,462,062 A | 10/1995 | Rubinstein et al. | 5,700,250 A | 12/1997 | Erskine |
| 5,466,223 A | 11/1995 | Bressler et al. | 5,702,080 A | 12/1997 | Whittier et al. |
| 5,471,992 A | 12/1995 | Banik et al. | 5,702,369 A | 12/1997 | Mercereau |
| 5,473,629 A | 12/1995 | Muramoto | 5,706,824 A | 1/1998 | Whittier |
| 5,476,099 A | 12/1995 | Robinson et al. | 5,707,392 A | 1/1998 | Kortenbach |
| 5,476,102 A | 12/1995 | Como et al. | 5,713,368 A | 2/1998 | Leigh |
| 5,478,313 A | 12/1995 | White | 5,713,888 A | 2/1998 | Neuenfeldt et al. |
| 5,480,385 A | 1/1996 | Thorne et al. | 5,715,832 A | 2/1998 | Koblish et al. |
| 5,482,054 A | 1/1996 | Slater et al. | 5,718,688 A | 2/1998 | Wozencroft |

| | | | | | | |
|---|---|---|---|---|---|---|
| 5,722,422 A | 3/1998 | Palmer et al. | | 6,001,080 A | 12/1999 | Kuracina et al. |
| 5,730,150 A | 3/1998 | Peppel et al. | | 6,004,294 A | 12/1999 | Brimhall et al. |
| 5,730,724 A | 3/1998 | Plishka et al. | | 6,007,560 A | 12/1999 | Gottlieb et al. |
| 5,735,827 A | 4/1998 | Adwers | | 6,015,391 A | 1/2000 | Rishton et al. |
| 5,738,660 A | 4/1998 | Luther | | 6,022,324 A | 2/2000 | Skinner |
| 5,738,665 A | 4/1998 | Caizza | | 6,024,708 A | 2/2000 | Bales et al. |
| 5,746,753 A | 5/1998 | Sullivan et al. | | 6,024,727 A | 2/2000 | Thorne et al. |
| 5,752,923 A | 5/1998 | Terwilliger | | 6,033,369 A | 3/2000 | Goldenberg |
| D395,609 S | 6/1998 | Knieriem et al. | | 6,036,361 A | 3/2000 | Gregory et al. |
| 5,758,655 A | 6/1998 | Como Rodriguez et al. | | 6,036,675 A | 3/2000 | Thorne et al. |
| 5,776,157 A | 7/1998 | Thorne et al. | | 6,047,729 A | 4/2000 | Hollister et al. |
| 5,795,336 A | 8/1998 | Romano et al. | | 6,050,954 A | 4/2000 | Mittermeier |
| 5,807,275 A | 9/1998 | Jamshidi | | 6,050,976 A | 4/2000 | Thorne et al. |
| 5,807,277 A | 9/1998 | Swaim | | 6,053,877 A | 4/2000 | Banik et al. |
| 5,810,744 A | 9/1998 | Chu et al. | | 6,063,037 A | 5/2000 | Mittermeier et al. |
| 5,817,069 A | 10/1998 | Arnett | | 6,063,040 A | 5/2000 | Owen et al. |
| 5,823,970 A | 10/1998 | Terwilliger | | 6,071,284 A | 6/2000 | Fox |
| 5,823,971 A | 10/1998 | Robinson et al. | | 6,080,115 A | 6/2000 | Rubinstein |
| 5,823,997 A | 10/1998 | Thorne | | 6,083,176 A | 7/2000 | Terwilliger |
| 5,824,002 A | 10/1998 | Gentelia et al. | | 6,083,202 A | 7/2000 | Smith |
| D400,806 S | 11/1998 | Tillack | | 6,086,563 A | 7/2000 | Moulton et al. |
| D400,808 S | 11/1998 | Schwan | | 6,090,078 A | 7/2000 | Erskine |
| 5,836,917 A | 11/1998 | Thorne et al. | | 6,090,108 A | 7/2000 | McBrayer et al. |
| 5,836,921 A | 11/1998 | Mahurkar | | 6,095,967 A | 8/2000 | Black et al. |
| 5,840,044 A | 11/1998 | Dassa et al. | | 6,096,005 A | 8/2000 | Botich |
| 5,843,001 A | 12/1998 | Goldenberg | | 6,102,920 A | 8/2000 | Sullivan et al. |
| 5,848,692 A | 12/1998 | Thorne et al. | | 6,106,484 A | 8/2000 | Terwilliger |
| 5,853,393 A | 12/1998 | Bogert | | 6,110,128 A | 8/2000 | Andelin et al. |
| 5,860,955 A | 1/1999 | Wright et al. | | 6,110,129 A | 8/2000 | Terwilliger |
| 5,865,806 A | 2/1999 | Howell | | 6,110,176 A | 8/2000 | Shapira |
| 5,871,453 A | 2/1999 | Banik et al. | | RE36,885 E | 9/2000 | Blecher et al. |
| 5,873,886 A | 2/1999 | Larsen et al. | | 6,117,108 A | 9/2000 | Woehr et al. |
| 5,879,332 A | 3/1999 | Schwemberger et al. | | 6,117,112 A | 9/2000 | Mahurkar |
| 5,879,337 A | 3/1999 | Kuracina et al. | | 6,117,115 A | 9/2000 | Hill et al. |
| 5,879,338 A | 3/1999 | Mahurkar | | 6,132,401 A | 10/2000 | Van Der Meyden |
| 5,882,337 A | 3/1999 | Bogert et al. | | 6,135,110 A | 10/2000 | Roy |
| 5,885,226 A | 3/1999 | Rubinstein et al. | | 6,142,956 A | 11/2000 | Kortenbach et al. |
| 5,891,105 A | 4/1999 | Mahurkar | | 6,142,957 A | 11/2000 | Diamond et al. |
| 5,893,845 A | 4/1999 | Newby | | 6,149,629 A | 11/2000 | Wilson et al. |
| 5,893,876 A | 4/1999 | Turkel et al. | | 6,171,284 B1 | 1/2001 | Kao |
| 5,895,361 A | 4/1999 | Turturro | | 6,174,292 B1 | 1/2001 | Kortenbach et al. |
| 5,897,507 A | 4/1999 | Kortenbach et al. | | 6,193,671 B1 | 2/2001 | Turturro et al. |
| 5,906,594 A | 5/1999 | Scarfone et al. | | 6,197,007 B1 | 3/2001 | Thorne et al. |
| 5,910,130 A | 6/1999 | Caizza et al. | | 6,203,527 B1 | 3/2001 | Zadini |
| 5,910,132 A | 6/1999 | Schultz | | 6,210,373 B1 | 4/2001 | Allmon |
| 5,911,705 A | 6/1999 | Howell | | 6,217,556 B1 | 4/2001 | Ellingson et al. |
| 5,913,859 A | 6/1999 | Shapira | | 6,221,029 B1 | 4/2001 | Mathis et al. |
| 5,916,175 A | 6/1999 | Bauer | | 6,221,047 B1 | 4/2001 | Greene et al. |
| 5,928,162 A | 7/1999 | Giurtino et al. | | 6,224,569 B1 | 5/2001 | Brimhall |
| 5,928,163 A | 7/1999 | Roberts et al. | | 6,224,576 B1 | 5/2001 | Thorne et al. |
| 5,928,200 A | 7/1999 | Thorne et al. | | 6,234,773 B1 | 5/2001 | Hill et al. |
| 5,935,109 A | 8/1999 | Donnan | | 6,254,575 B1 | 7/2001 | Thorne, Jr. et al. |
| 5,947,930 A | 9/1999 | Schwemberger et al. | | 6,261,242 B1 | 7/2001 | Roberts et al. |
| 5,951,489 A | 9/1999 | Bauer | | 6,264,617 B1 | 7/2001 | Bales et al. |
| 5,951,525 A | 9/1999 | Thorne et al. | | D446,135 S | 8/2001 | Chen |
| 5,951,582 A | 9/1999 | Thorne et al. | | 6,280,399 B1 | 8/2001 | Rossin et al. |
| 5,954,696 A | 9/1999 | Ryan | | 6,280,401 B1 | 8/2001 | Mahurkar |
| 5,954,698 A | 9/1999 | Pike | | 6,280,419 B1 | 8/2001 | Vojtasek |
| 5,957,863 A | 9/1999 | Koblish et al. | | 6,280,420 B1 | 8/2001 | Ferguson et al. |
| 5,957,887 A | 9/1999 | Osterlind et al. | | D448,314 S | 9/2001 | Chen |
| 5,957,892 A | 9/1999 | Thorne | | 6,283,925 B1 | 9/2001 | Terwilliger |
| 5,961,526 A | 10/1999 | Chu et al. | | 6,287,278 B1 | 9/2001 | Woehr et al. |
| 5,961,534 A | 10/1999 | Banik et al. | | 6,293,700 B1 | 9/2001 | Lund et al. |
| 5,964,717 A | 10/1999 | Gottlieb et al. | | 6,302,852 B1 | 10/2001 | Fleming, III et al. |
| 5,967,490 A | 10/1999 | Pike | | 6,309,376 B1 | 10/2001 | Alesi |
| 5,976,115 A | 11/1999 | Parris et al. | | 6,312,394 B1 | 11/2001 | Fleming, III |
| 5,979,840 A | 11/1999 | Hollister et al. | | 6,315,737 B1 | 11/2001 | Skinner |
| 5,980,488 A | 11/1999 | Thorne | | 6,321,782 B1 | 11/2001 | Hollister |
| 5,989,196 A | 11/1999 | Chu et al. | | 6,322,537 B1 | 11/2001 | Chang |
| 5,989,229 A | 11/1999 | Chiappetta | | 6,328,701 B1 | 12/2001 | Terwilliger |
| 5,989,241 A | 11/1999 | Plishka et al. | | 6,328,713 B1 | 12/2001 | Hollister |
| 5,993,426 A | 11/1999 | Hollister | | 6,334,857 B1 | 1/2002 | Hollister et al. |
| 6,000,846 A | 12/1999 | Gregory et al. | | 6,336,915 B1 | 1/2002 | Scarfone et al. |

| | | | | | | |
|---|---|---|---|---|---|---|
| 6,340,351 B1 | 1/2002 | Goldenberg | | 6,755,793 B2 | 6/2004 | Lamoureux et al. |
| 6,358,252 B1 | 3/2002 | Shapira | | 6,761,704 B2 | 7/2004 | Crawford |
| 6,358,265 B1 | 3/2002 | Thorne, Jr. et al. | | 6,761,706 B2 | 7/2004 | Vaillancourt |
| 6,361,525 B2 | 3/2002 | Capes et al. | | 6,764,567 B2 | 7/2004 | Sperko et al. |
| 6,379,333 B1 | 4/2002 | Brimhall et al. | | 6,767,336 B1 | 7/2004 | Kaplan |
| 6,379,338 B1 | 4/2002 | Garvin | | 6,770,050 B2 | 8/2004 | Epstein |
| 6,383,144 B1 | 5/2002 | Mooney | | 6,770,053 B2 | 8/2004 | Scarfone et al. |
| 6,406,459 B1 | 6/2002 | Allmon | | 6,796,962 B2 | 9/2004 | Ferguson et al. |
| 6,409,701 B1 | 6/2002 | Cohn et al. | | 6,798,348 B1 | 9/2004 | Wilker et al. |
| 6,416,484 B1 | 7/2002 | Miller et al. | | 6,811,308 B2 | 11/2004 | Chapman |
| 6,423,034 B2 | 7/2002 | Scarfone et al. | | 6,821,267 B2 | 11/2004 | Veillon, Jr. et al. |
| 6,439,768 B1 | 8/2002 | Wu et al. | | 6,827,488 B2 | 12/2004 | Knieriem et al. |
| 6,443,910 B1 | 9/2002 | Krueger et al. | | 6,832,990 B2 | 12/2004 | Kortenbach et al. |
| 6,443,927 B1 | 9/2002 | Cook | | 6,832,992 B2 | 12/2004 | Wilkinson |
| 6,443,929 B1 | 9/2002 | Kuracina et al. | | 6,839,651 B2 | 1/2005 | Lantz et al. |
| 6,478,751 B1 | 11/2002 | Krueger et al. | | 6,846,314 B2 | 1/2005 | Shapira |
| 6,485,468 B2 | 11/2002 | Vojtasek | | 6,849,051 B2 | 2/2005 | Sramek et al. |
| 6,485,473 B1 | 11/2002 | Lynn | | 6,855,128 B2 | 2/2005 | Swenson |
| 6,488,663 B1 | 12/2002 | Steg | | 6,855,130 B2 | 2/2005 | Saulenas et al. |
| 6,500,129 B1 | 12/2002 | Mahurkar | | 6,860,871 B2 | 3/2005 | Kuracina et al. |
| 6,501,384 B2 | 12/2002 | Chapman | | 6,875,183 B2 | 4/2005 | Cervi |
| 6,517,516 B1 | 2/2003 | Caizza | | 6,890,308 B2 | 5/2005 | Islam |
| 6,519,569 B1 | 2/2003 | White et al. | | 6,902,546 B2 | 6/2005 | Ferguson |
| 6,520,938 B1 | 2/2003 | Funderburk | | 6,916,292 B2 | 7/2005 | Morawski et al. |
| 6,537,255 B1 | 3/2003 | Raines | | 6,916,311 B2 | 7/2005 | Vojtasek |
| 6,537,259 B1 | 3/2003 | Niermann | | 6,916,314 B2 | 7/2005 | Schneider |
| 6,544,194 B1 | 4/2003 | Kortenbach et al. | | 6,923,813 B2 | 8/2005 | Phillips et al. |
| 6,551,287 B2 | 4/2003 | Hollister | | 6,936,036 B2 | 8/2005 | Wilkinson |
| 6,551,328 B2 | 4/2003 | Kortenbach | | D512,506 S | 12/2005 | Layne et al. |
| 6,554,778 B1 | 4/2003 | Fleming, III | | D512,924 S | 12/2005 | Ikeda |
| 6,569,125 B2 | 5/2003 | Jepson et al. | | 6,976,783 B2 | 12/2005 | Chen |
| 6,575,919 B1 | 6/2003 | Feiley et al. | | 6,981,948 B2 | 1/2006 | Peilegrino et al. |
| 6,582,402 B1 | 6/2003 | Erskine | | 6,984,213 B2 | 1/2006 | Horner et al. |
| 6,582,446 B1 | 6/2003 | Marchosky | | 6,989,003 B2 | 1/2006 | Wing et al. |
| 6,585,704 B2 | 7/2003 | Luther et al. | | 7,008,402 B2 | 3/2006 | Ferguson et al. |
| 6,592,556 B1 | 7/2003 | Thorne | | 7,018,343 B2 | 3/2006 | Plishka |
| 6,595,954 B1 | 7/2003 | Luther | | 7,021,824 B2 | 4/2006 | Wawro et al. |
| 6,595,955 B2 | 7/2003 | Ferguson et al. | | 7,033,324 B2 | 4/2006 | Giusti et al. |
| 6,613,018 B2 | 9/2003 | Bagga et al. | | 7,036,984 B2 | 5/2006 | Penney et al. |
| 6,616,604 B1 | 9/2003 | Bass et al. | | 7,063,703 B2 | 6/2006 | Reo |
| 6,616,630 B1 | 9/2003 | Woehr et al. | | 7,112,191 B2 | 9/2006 | Daga |
| 6,623,458 B2 | 9/2003 | Woehr et al. | | 7,118,552 B2 | 10/2006 | Shaw |
| 6,626,850 B1 | 9/2003 | Chau et al. | | 7,207,973 B2 | 4/2007 | Barrelle |
| D480,977 S | 10/2003 | Wawro et al. | | 7,226,434 B2 | 6/2007 | Carlyon et al. |
| D481,321 S | 10/2003 | Knieriem et al. | | 7,238,169 B2 | 7/2007 | Takagi et al. |
| 6,629,959 B2 | 10/2003 | Kuracina et al. | | 7,247,148 B2 | 7/2007 | Murashita |
| 6,634,789 B2 | 10/2003 | Babkes | | 7,255,475 B2 | 8/2007 | Quinn et al. |
| 6,635,033 B1 | 10/2003 | Hill et al. | | 7,264,613 B2 | 9/2007 | Woehr et al. |
| 6,638,252 B2 | 10/2003 | Moulton | | 7,300,420 B2 | 11/2007 | Doyle |
| 6,638,254 B2 | 10/2003 | Nakagami | | 7,303,548 B2 | 12/2007 | Rhad et al. |
| 6,641,562 B1 | 11/2003 | Peterson | | 7,316,507 B2 | 1/2008 | Sisk et al. |
| 6,652,486 B2 | 11/2003 | Bialecki et al. | | 7,357,784 B2 | 4/2008 | Ferguson |
| 6,652,490 B2 | 11/2003 | Howell | | 7,377,908 B2 | 5/2008 | Buetikofer et al. |
| 6,663,592 B2 | 12/2003 | Rhad et al. | | 7,488,306 B2 | 2/2009 | Nguyen |
| 6,673,047 B2 | 1/2004 | Crawford | | 7,500,965 B2 | 3/2009 | Menzi et al. |
| 6,673,060 B1 | 1/2004 | Fleming, III | | 7,513,888 B2 | 4/2009 | Sircom |
| 6,682,510 B2 | 1/2004 | Niermann | | 2001/0021827 A1 | 9/2001 | Ferguson et al. |
| 6,689,102 B2 | 2/2004 | Greene | | 2002/0021827 A1 | 2/2002 | Smith |
| 6,692,471 B2 | 2/2004 | Boudreaux | | 2003/0002562 A1 | 1/2003 | Yerlikaya et al. |
| 6,695,814 B2 | 2/2004 | Greene et al. | | 2003/0100868 A1 | 5/2003 | Ferguson et al. |
| 6,698,921 B2 | 3/2004 | Siefert | | 2003/0114797 A1 | 6/2003 | Vaillancourt et al. |
| 6,699,221 B2 | 3/2004 | Vaillancourt | | 2003/0144627 A1 | 7/2003 | Woehr et al. |
| 6,702,786 B2 | 3/2004 | Olovson | | 2003/0176810 A1 | 9/2003 | Maahs et al. |
| 6,709,419 B2 | 3/2004 | Woehr | | 2003/0191438 A1 | 10/2003 | Ferguson et al. |
| 6,719,732 B2 | 4/2004 | Courteix | | 2003/0220617 A1 | 11/2003 | Dickerson |
| 6,723,075 B2 | 4/2004 | Davey et al. | | 2004/0071182 A1 | 4/2004 | Quinn et al. |
| 6,727,805 B2 | 4/2004 | Hollister et al. | | 2004/0077973 A1 | 4/2004 | Groenke et al. |
| 6,730,043 B2 | 5/2004 | Krueger et al. | | 2004/0078003 A1 | 4/2004 | Smith et al. |
| 6,731,216 B2 | 5/2004 | Ho et al. | | 2004/0078007 A1 | 4/2004 | Nguyen |
| 6,740,063 B2 | 5/2004 | Lynn | | 2004/0092889 A1 | 5/2004 | Ferguson et al. |
| 6,749,576 B2 | 6/2004 | Bauer | | 2004/0133167 A1 | 7/2004 | Ferguson et al. |
| 6,749,588 B1 | 6/2004 | Howell et al. | | 2004/0153005 A1 | 8/2004 | Krueger |
| 6,749,595 B1 | 6/2004 | Murphy | | 2004/0162536 A1 | 8/2004 | Vaillancourt |

| | | |
|---|---|---|
| 2004/0171989 A1 | 9/2004 | Horner et al. |
| 2004/0186434 A1 | 9/2004 | Harding et al. |
| 2004/0225260 A1 | 11/2004 | Villa et al. |
| 2004/0236288 A1 | 11/2004 | Howell et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0090763 A1 | 4/2005 | Wang |
| 2005/0090764 A1 | 4/2005 | Wang |
| 2005/0113716 A1 | 5/2005 | Mueller, Jr. et al. |
| 2005/0119652 A1 | 6/2005 | Vetter et al. |
| 2005/0131345 A1 | 6/2005 | Miller |
| 2005/0137500 A1 | 6/2005 | Wingler |
| 2005/0165404 A1 | 7/2005 | Miller |
| 2005/0192536 A1 | 9/2005 | Takagi et al. |
| 2005/0203459 A1 | 9/2005 | Alchas |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0097345 A1 | 4/2008 | Ferguson |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| EP | 1358846 A1 | 11/2003 |
| JP | 6-241914 A | 9/1994 |
| WO | 96-22800 A1 | 8/1996 |
| WO | 97-42989 A1 | 11/1997 |
| WO | 2004060138 A2 | 7/2004 |
| WO | 2004091687 A2 | 10/2004 |
| WO | 2005009246 A1 | 2/2005 |
| WO | 2005053774 A1 | 6/2005 |
| WO | WO 2005053774 A1 * | 6/2005 |
| WO | 2005060679 A2 | 7/2005 |

OTHER PUBLICATIONS

Office action dated Feb. 4, 2010 from related U.S. Appl. No. 11/179,438, 7 pgs.

All prosecution related to U.S. Appl. No. 11/179,438, filed Jul. 11, 2005.

All prosecution related to U.S. Appl. No. 11/7179,696, filed Jul. 11, 2005.

* cited by examiner

SAFETY RESET KEY AND NEEDLE ASSEMBLY

BACKGROUND OF THE INVENTION

This invention relates generally to needle assemblies and more particularly to needle assemblies that have shields to cover sharp ends of needles.

Needle assemblies of the present invention have particular, although not exclusive application in the field of medicine and have needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle.

In cases where a sample (e.g., a bone marrow sample) is collected by the needle assembly, the sample has to be removed from the needle assembly. An obturator is a device including a long thin shaft, and in some cases includes a blunt tip, that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for second use, but which will not result in inadvertent release of the safety shield.

SUMMARY OF THE INVENTION

In one aspect of the present invention, a needle assembly generally comprises mounting structure and a needle mounted on the mounting structure and extending outwardly therefrom. The needle has a longitudinal axis, a sharp end and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. The tubular housing has distal and proximal ends and at least one peripheral slot extending radially inwardly from the periphery and axially along the housing from the distal end of the housing. A reset key adapted to actuate release of the locking mechanism to permit the shield to be moved relative to the needle comprises a support and at least one rib on the support sized and arranged for reception in the peripheral slot of the tubular housing for entering the tubular housing to actuate release of the locking mechanism.

In another aspect of the present invention, a reset key for use in releasing a locking mechanism of a safety shield covering a sharp tip of a needle for movement of the safety shield relative to the needle generally comprises a support defining a central open space sized and shaped for receiving at least a portion of the safety shield. Ribs mounted on the support and located at positions spaced circumferentially of each other generally around the perimeter of the central open space are shaped and arranged for reception in slots on the safety shield when the safety shield is received in the central open space for actuating release of the locking mechanism.

In yet another aspect of the present invention, a reset key for use in releasing a locking mechanism of a safety shield covering a sharp tip of a needle for movement of the safety shield relative to the needle generally comprises a shroud sized and shaped for receiving at least a majority of the safety shield therein. A reset member associated with the shroud can actuate release of the locking mechanism when the safety shield is received in the shroud.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
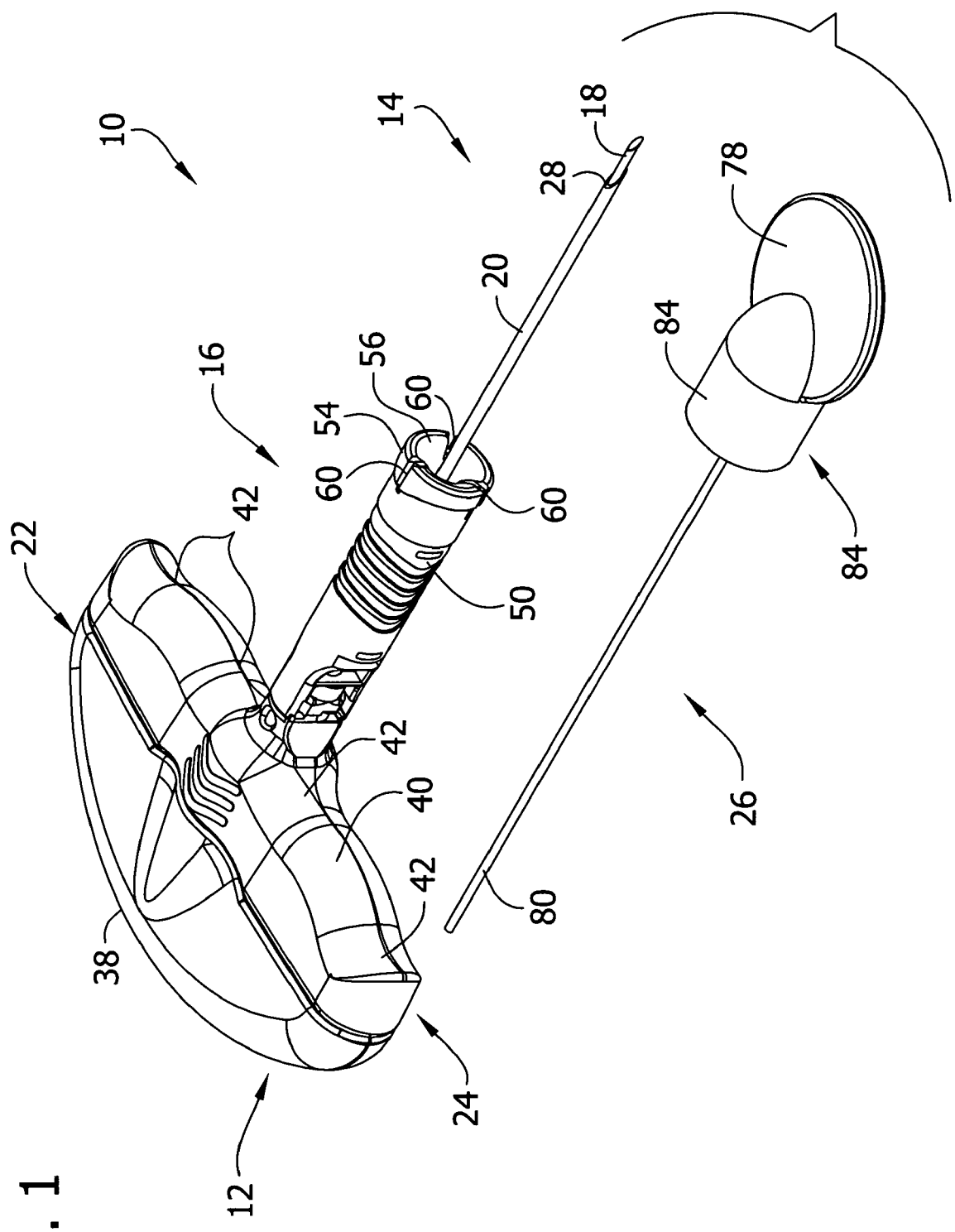
FIG. 1 is a perspective of a bone needle assembly including an obturator.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure"), a needle 14 and a cannula safety shield 16, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for a needle can be other than a handle without departing from the present invention. The needle assembly 10 further includes an obturator 26, which is described more fully below, that may be used to remove a sample captured in the cannula 20.

The cannula 20 has a central axial passage extending the length of the cannula and opening at both ends of the cannula. A distal tip 28 of the cannula 20 is beveled and sharpened, and a proximal end portion of the cannula 20 is received in the distal handle member 24. The stylet 18 is solid and includes a sharp distal tip, and a proximal end portion of the stylet is received in the proximal handle member 22. The stylet 18 can be inserted through the central axial passage opening in the proximal end portion of the cannula 20 and received entirely through the axial passage of the cannula so that its sharp distal tip projects axially outward from the distal tip 28 of the cannula (as shown in FIG. 1). The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 42 for receiving the technician's fingers. The form of the handle can be other than described herein without departing from the scope of the present invention. Moreover, needle mounting structure can be other than a handle within the scope of the present invention. The proximal and distal handle members 22, 24 can be connected together in a suitable manner when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

The cannula safety shield 16 may be moved to cover the distal tip 28 of the cannula 20 after the needle assembly 10 has been used. The safety shield 16 includes a generally tubular housing 50 and an internal locking mechanism (generally indicated at 52 in FIG. 2) capable of releasably locking the tubular housing in position covering the distal tip 28 of the cannula 20. The tubular housing 50 has a proximal end closer to the handle 12 and a distal end farther away from the handle. A distal end piece of the tubular housing 50 (generally indicated at 54) includes a funnel-shaped distal end surface 56 of the tubular housing 50 and a central aperture 58 generally aligned with the central axial passageway of the cannula 20. Although illustrated as a separately formed part attached to the tubular housing 50, the distal end piece 54 and tubular housing may be formed as a single piece of material. The shape of the distal end surface 56 may be other than described (e.g., lying in a plane perpendicular to the longitudinal axis of the cannula 20) within the scope of the present invention. Three slots 60 located on the periphery of the tubular housing distal end piece 54 each extend radially inwardly from the periphery of the end piece at its distal end and also extend axially along the end piece toward the proximal end of the tubular housing 50. The number of slots and their precise configuration may be other than described without departing from the scope of the present invention. The function of the slots 60 will be described hereinafter. The tubular housing 50 and handle 12 may include structure to secure the tubular housing in a retracted position adjacent the handle when not needed. An example of such structure is shown in co-assigned U.S. application Ser. No. 11/146,173, filed Jun. 6, 2005, the disclosure of which is incorporated herein by reference.

The locking mechanism 52 inside the safety shield 16 comprises a canting member including a base 62 having a hole and a pair of arms 64 (only one is shown) extending generally axially from the base. The arms 64 are connected together by a U-shaped member 66 at their ends and each has an upwardly (as oriented in the figures) bent tab 68 (only one is shown) projecting axially outward from the end. Before the locking mechanism 52 is activated to lock the tubular housing 50 in position, the ends of the arms 64 ride on the exterior surface of the cannula 20. This holds the canting member so that the base 62 is generally orthogonal so the longitudinal axis of the cannula 20 and the base can move along the cannula (with the safety shield 16), with the cannula sliding substantially unimpeded through the hole in the base. Once the ends of the arms 64 pass the distal tip 28 of the cannula 20, the locking mechanism 52 is constructed so that the ends of the arms move in a generally radial direction toward an opposite side of the longitudinal axis of the cannula 20. This causes the base 62 of the canting member to cant relative to the axis of the cannula 20 so that the hole in the base is no longer orthogonal to the axis of the cannula. As a result, the base 62 at the edge of the hole grippingly engages the cannula 20 to lock the safety shield 16 in place. The locking mechanism 52 further includes angled surfaces 69A, 69B fixed to the tubular housing 50 that can engage the canting member base 62 to keep the canting member in its canted, locking position upon movement of the tubular housing 50 in either direction relative to the cannula 20. It will be understood that a locking mechanism could take on other forms than shown and described without departing from the scope of the present invention.

The safety shield 16 further includes an annular reset plunger 70 located inside the tubular housing 50 near its distal end. The reset plunger 70 is movable axially relative to the housing 50 toward the proximal end and includes a frusto-conically shaped front surface 72 that is engageable with the tabs 68 of the locking mechanism to release the locking mechanism, as will be more fully described hereinafter. A spring 74 engages the reset plunger 70 and biases it toward the distal end of the tubular housing 50. Thus, unless the reset plunger 70 is forcibly moved, it normally does not interfere with the operation of the locking mechanism 52.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passageway of the cannula 20 while the cannula remains in the bone. In order to collect a sample of bone marrow, the distal handle member 24 is advanced further into the bone. The sharp tip 28 of the cannula 20 cuts into the bone marrow and a sample is received in the central axial passageway of the cannula. The cannula 20 can then be withdrawn from the patient by pulling on the distal handle member 24. The sample remains lodged in the central axial passageway of the cannula 20 near the sharp tip 28. It will be understood that a needle assembly may be used to collect a sample other than of bone marrow within the scope of the present invention. Moreover, it is not necessary that a cannula be used to collect any sample. For instance, the cannula could also be used to withdraw or infuse fluid.

Figure 6:
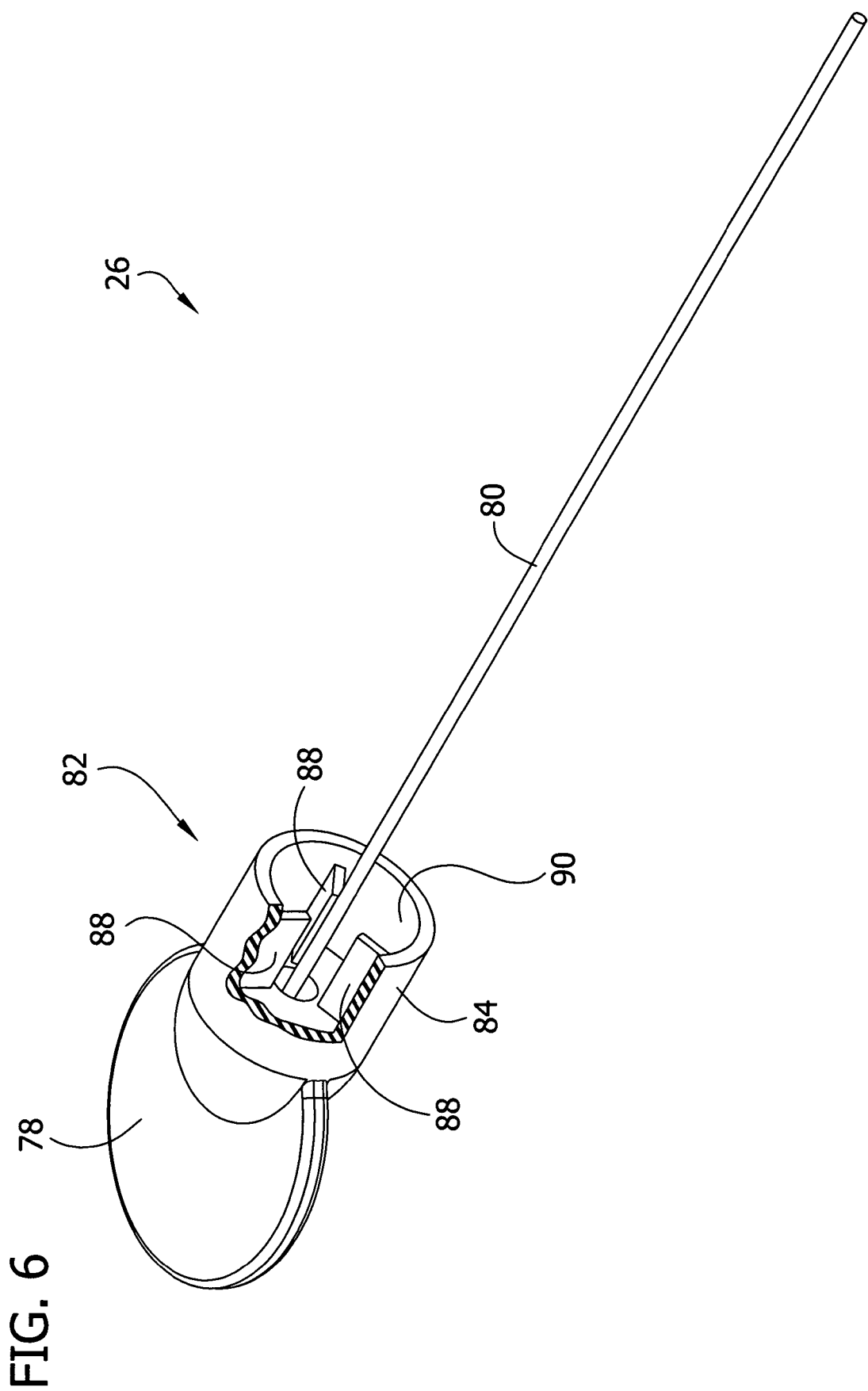
FIG. 6 is a fragmentary perspective of the obturator with parts broken away to show internal construction.
Figure 7:
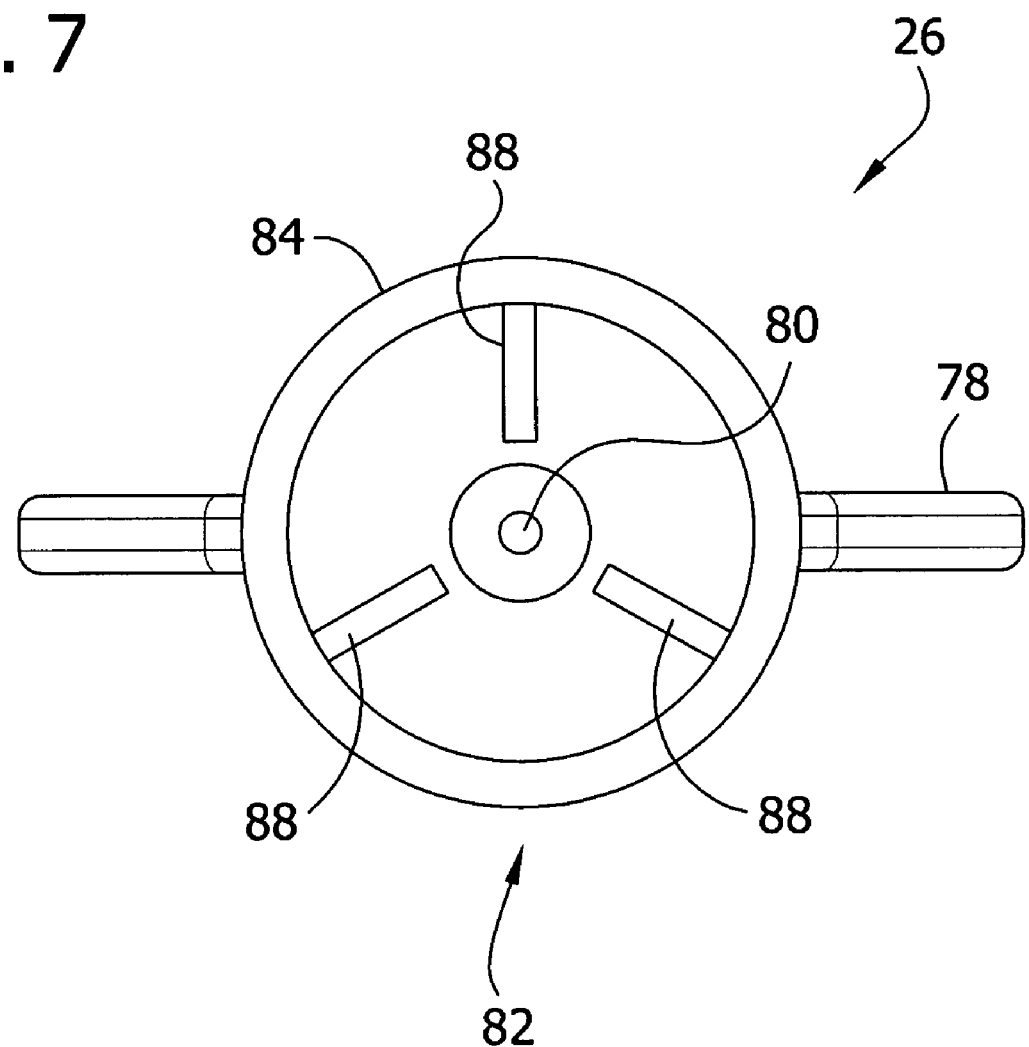
FIG. 7 is an end view of the obturator.
Figure 8:
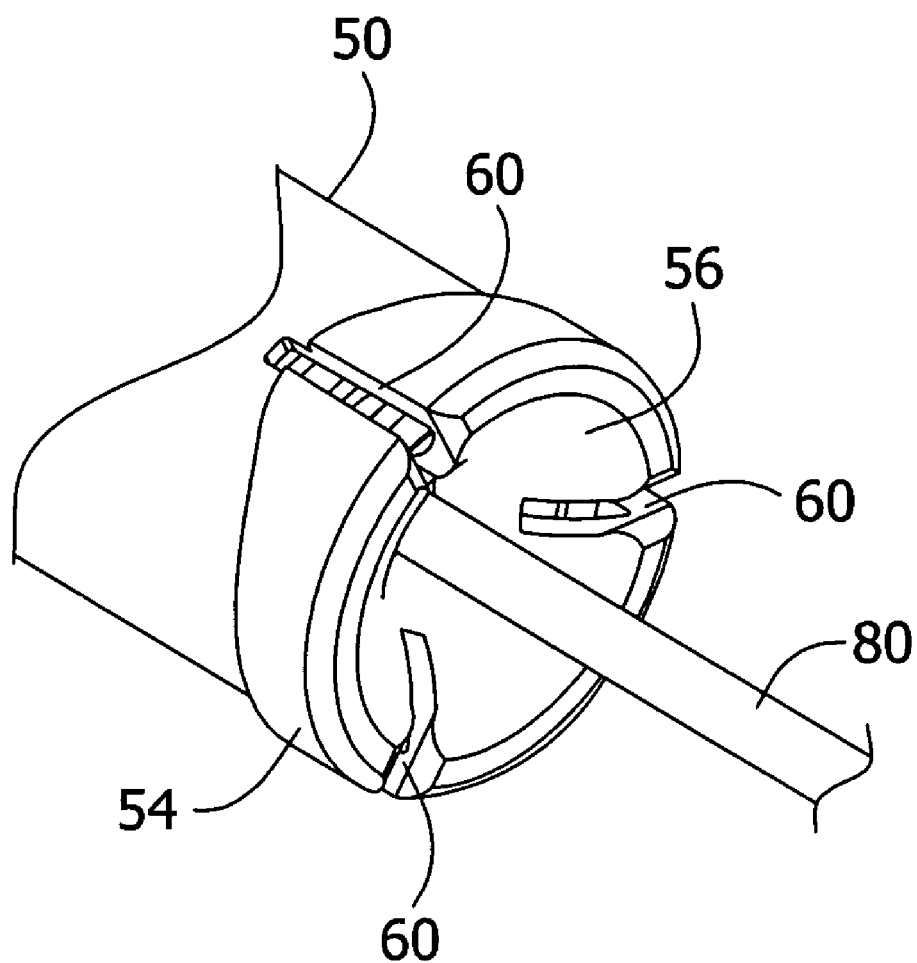
FIG. 8 is a fragmentary perspective of the obturator entering the safety shield.

The obturator 26 is used to remove a lodged sample of bone marrow that has been collected in the central axial passageway of cannula 20. The obturator 26 includes a grip 78 and a long, thin shaft 80 extending from the grip that is sized to be received in the central axial passageway of the cannula 20 in generally close fitting relation therein. The grip 78 is sized and shaped to be grasped by a user (e.g., between the thumb and pointer finger) for manipulating the obturator 26, as will be described. As shown best in FIGS. 6 and 7, a reset key, generally indicated 82, extends from the grip 78 in the same direction as the shaft 80, and as illustrated is formed as one piece of material with the grip. In the illustrated embodiment, the reset key 82 comprises a tubular shroud 84 (broadly, "a support") defining a central open space 86 sized and shaped to receive a portion of the tubular housing 50 therein. Although shown as a solid tubular piece of material with an open end, the shroud 84 need not be solid around its circumference within the scope of the present invention. Three elongate ribs 88 formed on an inner wall 90 of the tubular shroud 84 extend generally parallel to the axis of the shroud and are arranged for reception in the slots 60 of the tubular housing 50 as will be described. It will be appreciated that a reset key (not shown) may not be part of an obturator (i.e., the reset key would not include a shaft like shaft 80) without departing from the scope of the present invention.

Figure 2:
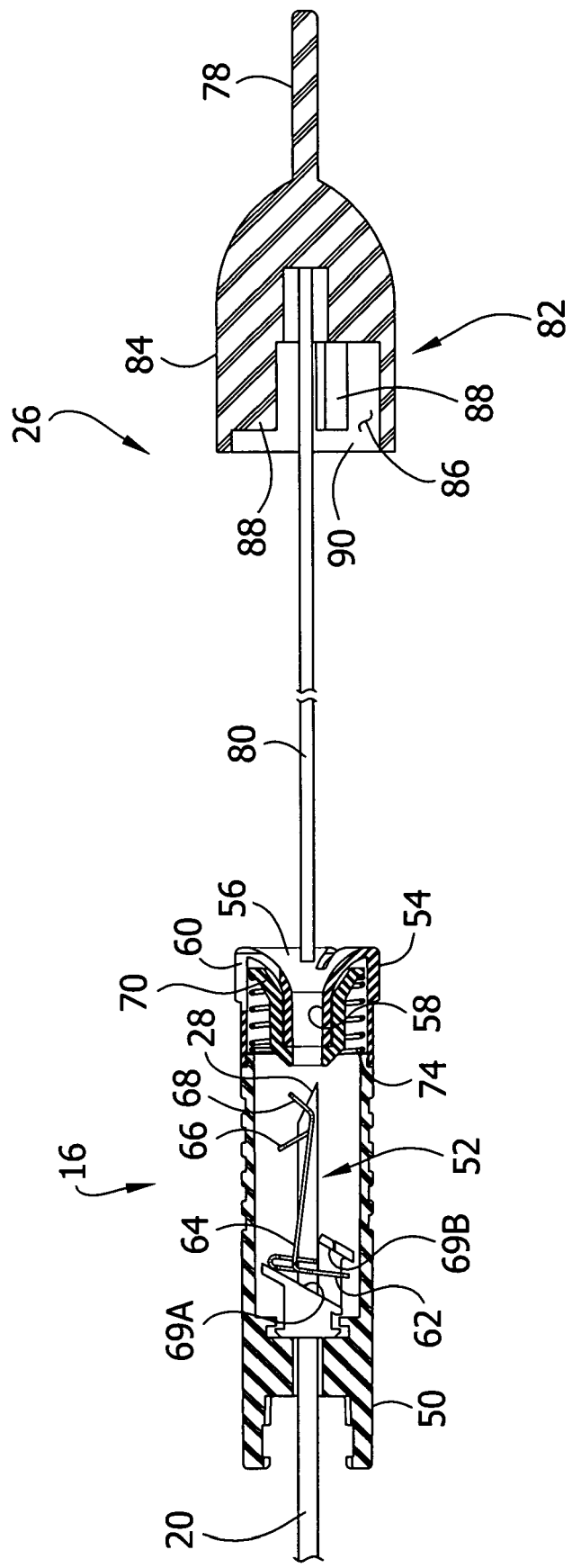
FIG. 2 is a fragmentary partial section of the needle assembly with the obturator entering a safety shield of the needle assembly.
Figure 3:
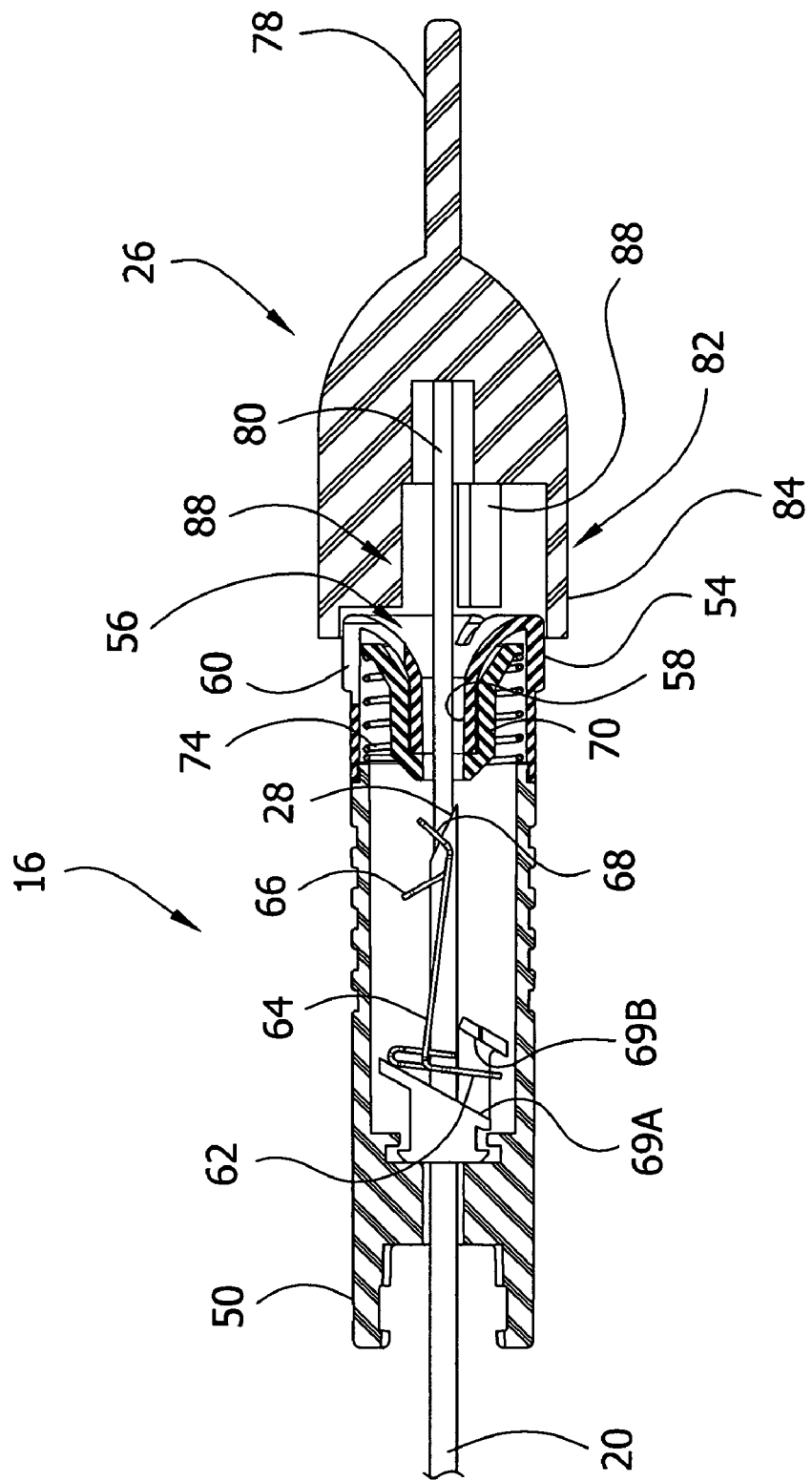
FIG. 3 is the fragmentary elevation of FIG. 2 but showing the obturator inserted to a position in which a sample collected by the needle assembly is pushed out of the needle assembly.

FIG. 2 illustrates the initial position of the obturator 26 with the shaft 80 entering the distal end of the tubular housing 50. The free end of the shaft 80 has not yet entered the central axial passageway of the cannula 20 or the aperture 58 of the distal end piece 54. The funnel-shaped surface 56 of the distal end piece 54 guides the shaft 80 toward the aperture 58 that is aligned with the central axial passageway of the cannula 20, thereby facilitating reception of the shaft in the passageway. The grip 78 is pushed to advance the shaft 80 through the aperture 58 in the funnel-shaped surface 56 and into the central axial passageway, which pushes the sample toward the proximal end of the central axial passageway. The shaft 80 is advanced until it protrudes out of the proximal end of the central axial passageway, thereby pushing the sample (not shown) out of the cannula 20 where it can be collected in a Petri dish or other suitable container. The relative location of the tubular shroud 84 and safety shield 16 are in this position are illustrated in FIG. 3. As the shaft 80 is advanced, it slides through the aperture 58 in the distal end piece 54. The locking mechanism 52 remains engaged so that the safety shield 16 does not move and the sharp tip 28 remains covered.

The technician may observe the sample ejected from the central axial passageway of the cannula 20. If it is determined that the sample is satisfactory, the obturator 26 can be pulled so that the shaft 80 slides back through and out of the cannula 20. The needle assembly 10 can be discarded, or possibly but less likely, cleaned and sterilized for a subsequent use. If the sample is not satisfactory, however, it will be necessary to obtain a second sample from the same patient. This can be done using the same needle assembly 10, but the tubular housing 50 is locked in place by the locking mechanism 52 over the sharp tip 28 of the cannula 20. The tubular housing 50 needs to be moved away from the tip 28 before the needle assembly 10 can be used to obtain a second sample.

The obturator 26 of the present invention is particularly adapted to permit the safety shield 16 to be released and moved back from the sharp tip 28 of the cannula 20. It should be understood, however, that a device other than an obturator 26 incorporating the resetting, or unlocking, features of the obturator described herein, but not functioning as an obturator, is also contemplated as within the scope of the present invention. From the position shown in FIG. 3, the grip 78 can be advanced toward the tubular housing 50 so that the ribs 88 are received into the corresponding peripheral slots 60 in the tubular housing 50. It will be necessary to align the ribs 88 with corresponding ones of the slots 60 before the ribs may enter the slots. The slots 60 and ribs 88 may be shaped and/or arranged to make this easier or harder to accomplish as desired. In the illustrated embodiment, the three slots 60 and three ribs 88 are all the same size and shape and located at 120 degree intervals. This arrangement makes it relatively easy to align the obturator 26 and safety shield 16 so that the ribs 88 will be received in the slots 60. However, as stated previously, other arrangements and configurations are envisioned. For example and without limiting the breadth of the present disclosure, the slots 60 and ribs 88 can be arranged at unequal intervals. Moreover, the slots 60 and ribs 88 may have different sizes so that the ribs will be received in the slots in only one relative orientation of the obturator 26 and the safety shield 16. Those of ordinary skill in the art will appreciate other possible configurations and/or arrangements. The bias of the spring 74 resists further advancement of the ribs 88 and hence of the obturator 26. This provides a tactile signal to the technician that the obturator shaft 80 has been inserted far enough into the central axial passageway of the cannula 20 to remove the sample, and that further insertion will result in release of the locking mechanism 52.

Figure 4:
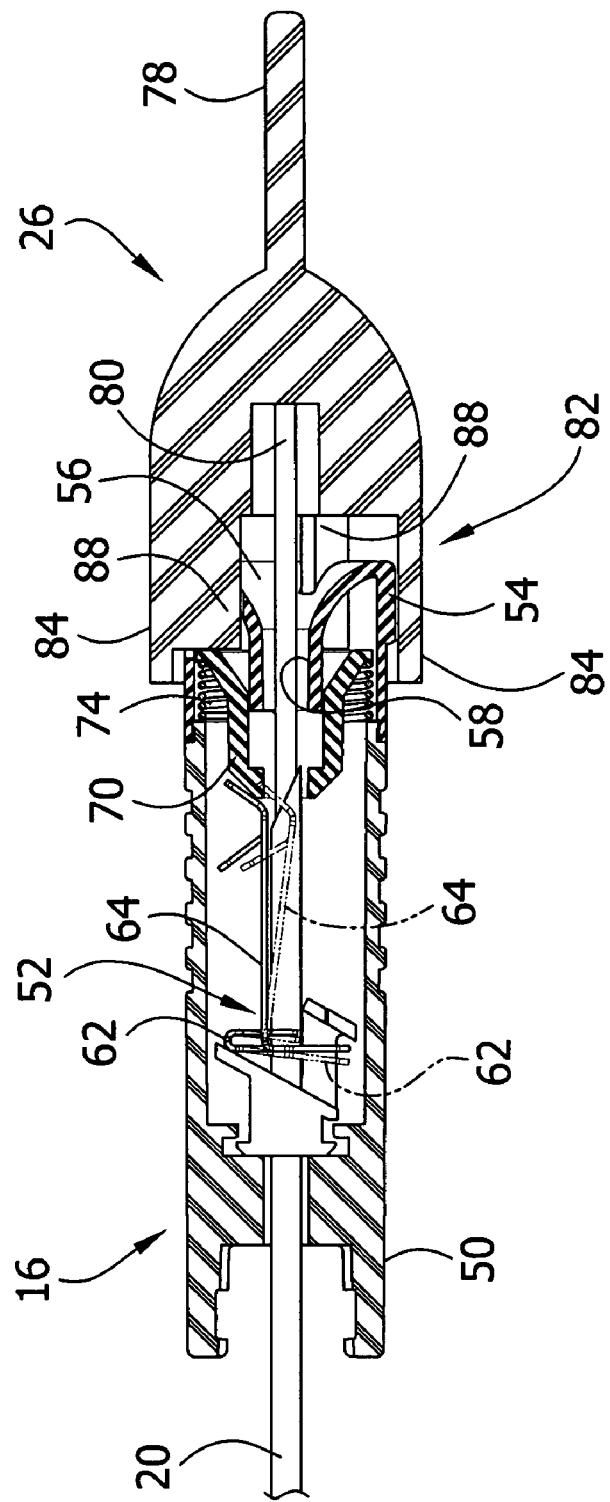
FIG. 4 is the fragmentary elevation of FIG. 2 but showing use of the obturator to reset a locking mechanism of the safety shield.
Figure 5:
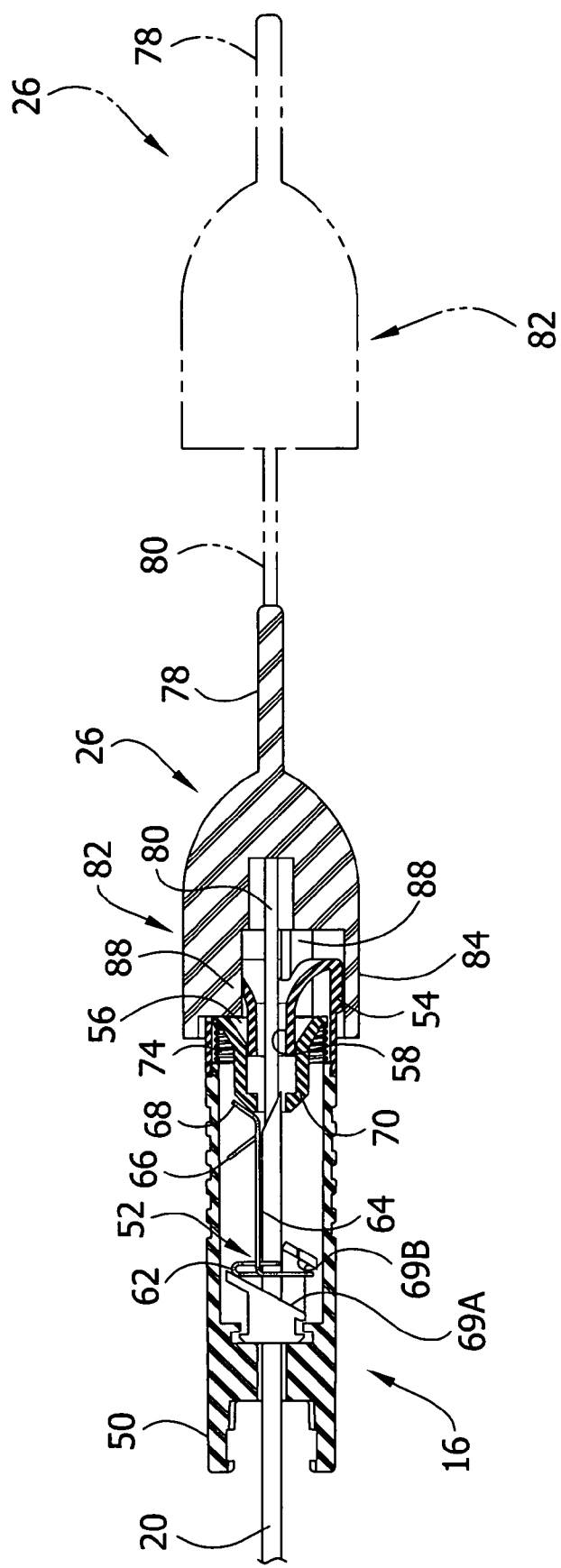
FIG. 5 is the fragmentary elevation of FIG. 2 but showing the safety shield set for withdrawal from a sharp end of the needle assembly after release of the locking mechanism.

If the safety shield 16 is to be reset to expose the sharp tip 28 of the cannula 28, the grip 78 can be advanced toward the tubular housing 50 so that the ribs 88 move into the slots 60 and push the reset plunger 70 against the bias of the spring 74 axially toward the proximal end of the tubular housing 50. The front surface 72 of the reset plunger 70 engages the tabs 68 of the canting member moving the arms 64 back to a position more nearly parallel to the longitudinal axis of the cannula 20. This moves the base 62 of the canting member to a position substantially orthogonal to the longitudinal axis of the cannula 20 so that the cannula can once again slide freely through the hole in the base (FIG. 4). The locking mechanism 52 is thereby released. Thus as shown in FIG. 5, the tubular housing 50 can be grasped to pull back the safety shield 16 toward the distal housing member 24 so that the sharp tip 28 of the cannula 20 is once again exposed. The obturator shaft 80 can be removed and the stylet 18 can be reinserted into the cannula 20 for a second collection of a sample. When the ribs 88 move back out of the slots 60, the spring 74 moves the reset plunger 70 back toward the distal end of the tubular housing 50 so that the locking mechanism 52 is again free to operate for locking the safety shield 16 over the sharp tip 28 of the cannula 20.

Figure 9:
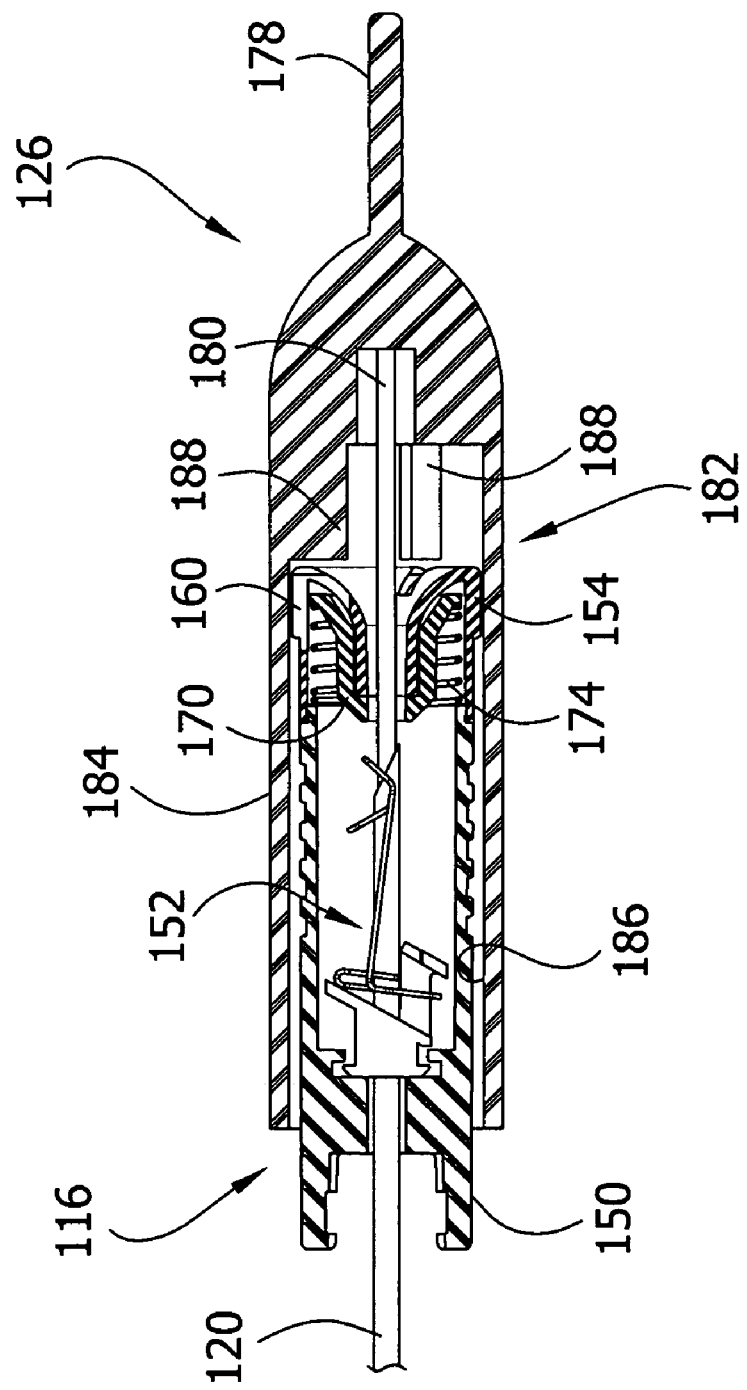
FIG. 9 is a fragmentary partial section of a needle assembly of a second embodiment in a configuration similar to FIG. 3.
Figure 10:
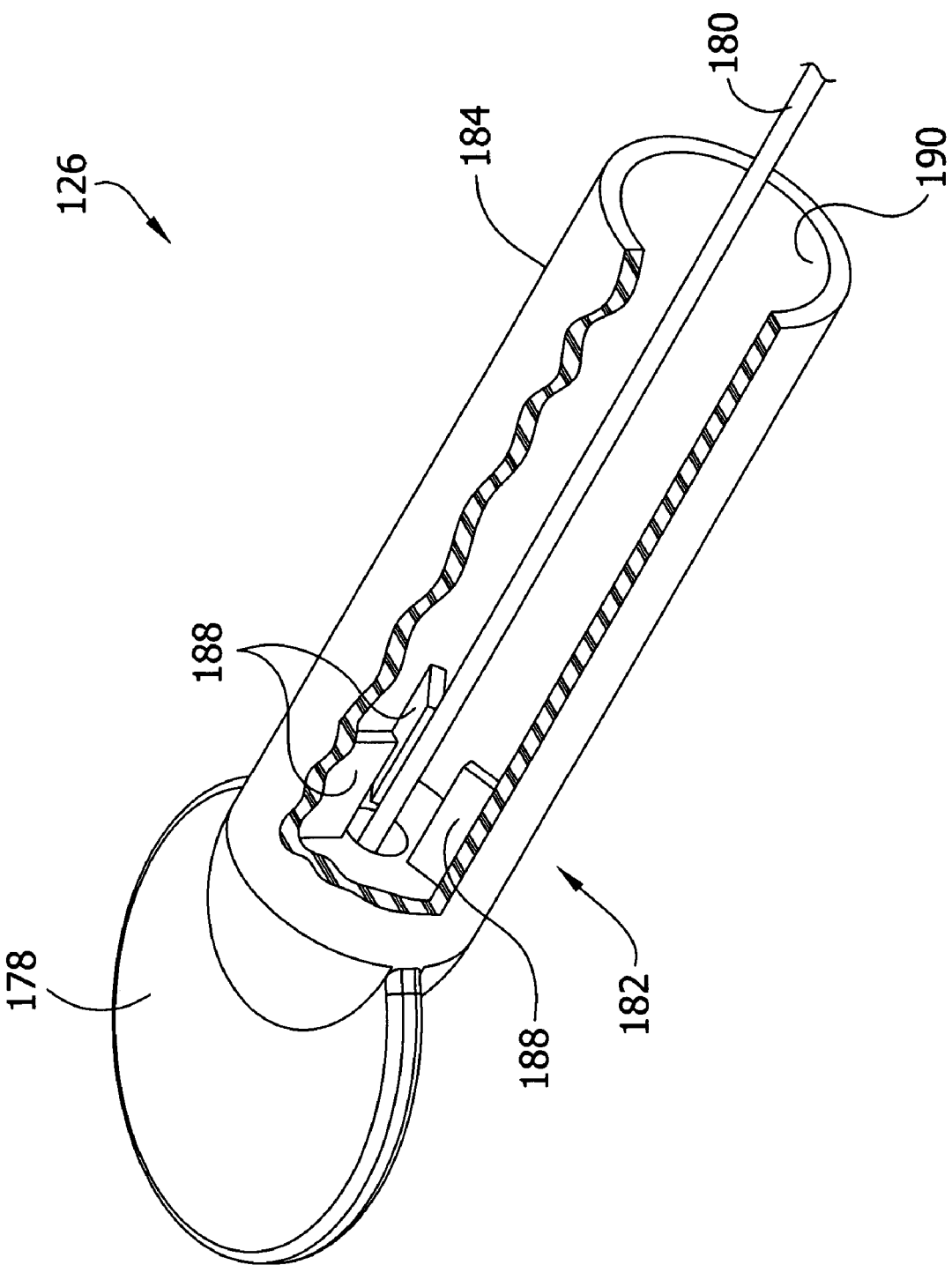
FIG. 10 is a fragmentary perspective of an obturator of the needle assembly of FIG. 9.
Figure 11:
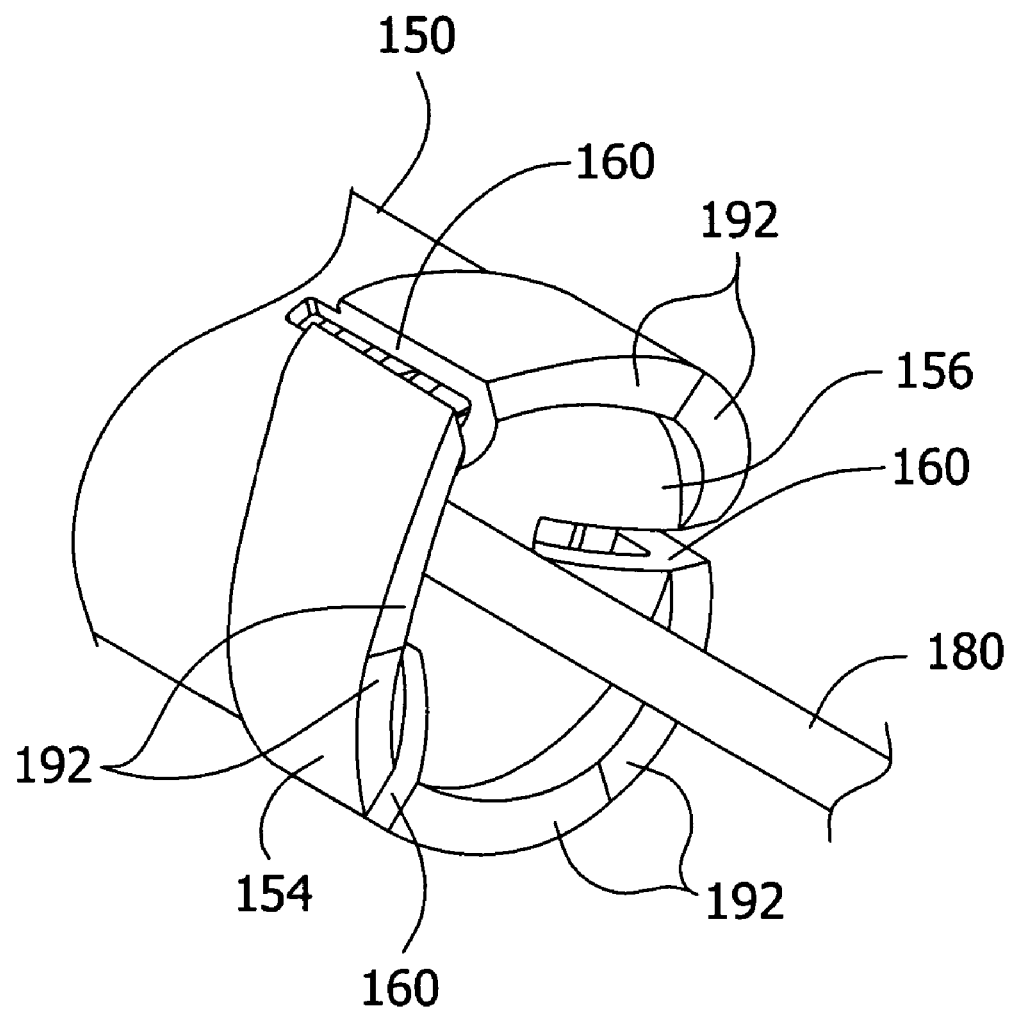
FIG. 11 is a fragmentary perspective of an end of a shield of the needle assembly of FIG. 9.

Referring now to FIGS. 9 and 10, a needle assembly of a second embodiment is shown. Parts of the needle assembly of the second embodiment are given the same reference numerals as the corresponding parts of the needle assembly of the first embodiment, plus "100". A safety shield 116 may have substantially the same construction as the safety shield 16. In particular, the shield 116 includes a tubular housing 150 having peripheral slots 160, as in the first embodiment. An obturator 126 and reset key 182 also have similar constructions (e.g., including ribs 188) as in the first embodiment. However, a tubular shroud 184 of the second embodiment has a length which is sufficiently great so that a central open space 186 of the shroud can receive substantially the entire tubular housing 150. Preferably at least a majority of the tubular housing 150 is received in the open space 186 of the shroud 184. The operation of ribs 188 associated with the tubular shroud 184 to release a locking mechanism 152 may be as described for the first embodiment. However by receiving tubular housing 150 in the central open space 186 of the shroud 184, the tubular housing is shielded from being inadvertently grasped as the obturator is pulled away from the safety shield so that the safety shield 116 is not unintentionally pulled off of the cannula 20. As best seen in FIG. 11, the peripheral edge of a distal end piece 154 of the tubular housing 150 is shaped to include edge segments 192 arranged at converging angles to funnel the ribs 188 into the slots 160 when the ribs engage the distal end piece. Because the ribs 188 are located deep inside the tubular shroud 184 at the bottom of the open space 186, alignment of the ribs with the slots 160 could be difficult. However, the shaped peripheral edge segments 192 engage the ribs 188 and urge the rotation of the obturator 126 to properly orient the reset key 182 so that the ribs move into the slots 160.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A needle assembly comprising:
   mounting structure;
   a needle mounted on the mounting structure and extending outwardly therefrom, the needle having a longitudinal axis, a sharp end and a central axial passageway;
   a safety shield associated with the needle comprising:
      a tubular housing adapted for movement relative to the needle between a stowed position in which the tubular housing is spaced from the sharp end of the needle and a deployed position in which the tubular housing covers the sharp end,
      a locking mechanism adapted to releasably lock the tubular housing in position covering the sharp end of the needle, the tubular housing having distal and proximal ends and at least one peripheral slot extending radially inward from the periphery and axially along the housing from the distal end of the housing; and
   a reset key adapted to actuate release of the locking mechanism to permit the shield to be moved relative to the needle, the reset key comprising:
      a support; and
      at least one rib on the support sized and arranged to be received in the peripheral slot of the tubular housing for entering the tubular housing to actuate release of the locking mechanism.

2. A needle assembly as set forth in claim 1 wherein:
   there is a plurality of peripheral slots located around the periphery of the tubular housing at the distal end; and
   the reset key comprises a rib for each of the plurality of peripheral slots.

3. A needle assembly as set forth in claim 2 wherein the safety shield further comprises an unlocking mechanism located in the tubular housing for engagement by the ribs of the reset key through the peripheral slots, the unlocking mechanism being movable axially in the tubular housing for engaging the locking mechanism to release the locking mechanism.

4. A needle assembly as set forth in claim 3 wherein the locking mechanism comprises a canting member including a base having a hole receiving the needle therethrough and an arm extending from the base, the base being arranged to permit the needle to slide freely through the hole in an unlocked position of the canting member, and being canted relative to the needle in a locked position for gripping the needle to lock the tubular housing in position in a locked position of the canting member.

5. A needle assembly as set forth in claim 4 wherein the arm and unlocking mechanism are shaped and arranged for engagement with each other to move the canting member from the locked position to the unlocked position upon actuation by the reset key.

6. A needle assembly as set forth in claims 1 further comprising an obturator including a shaft sized and shaped to be received in the central axial passageway of the needle, the reset key being associated with the obturator.

7. A needle assembly as set forth in claim 6 wherein the reset key support comprises a tubular shroud sized and shaped for receiving at least a majority of the tubular housing when the obturator shaft is inserted into the central axial passageway of the needle.

8. A needle assembly as set forth in claim 7 wherein the tubular shroud is sized for receiving a substantial entirety of the tubular housing.

9. A needle assembly as set forth in claim 7 wherein the rib is located on an inner wall of the tubular shroud 10. A reset key for use in releasing a locking mechanism of a safety shield covering a sharp tip of a needle permitting the safety shield to move relative to the needle, the reset key comprising:

a support defining a central open space sized and shaped for receiving at least a portion of the safety shield; and a plurality of ribs mounted on the support and located at positions spaced circumferentially from each other generally around a perimeter of the central open space, the ribs being shaped and arranged to be received in slots on the safety shield when the safety shield is received in the central open space for actuating release of the locking mechanism.

11. A reset key as set forth in claim 10 wherein the support comprises a tubular shroud, the ribs being formed as one piece with the shroud.

12. A reset key as set forth in claim 11 wherein the tubular shroud has a longitudinal axis and the ribs extend generally parallel to the longitudinal axis.

13. A reset key as set forth in claim 10 wherein the tubular shroud is sized for receiving a substantial entirety of the safety shield.

14. A reset key as set forth in claim 10 further comprising a shaft mounted on the support, the shaft being adapted to be received in a central axial passageway of the needle.

15. A reset key for releasing a locking mechanism of a safety shield covering a sharp tip of a needle permitting the safety shield to move relative to the needle, the reset key comprising:

a shroud selectively engageable with and disengageable from the safety shield sized and shaped for receiving at least a majority of the safety shield during engagement of the shroud and the safety shield; and a reset member positioned with respect to the shroud for actuating release of the locking mechanism of the safety shield covering the sharp tip of the needle when the safety shield is received in the shroud, permitting the safety shield to move relative to the needle to uncover the sharp tip of the needle.

16. A reset key as set forth in claim 15 wherein the shroud is sized for receiving a substantial entirety of the safety shield.

17. A reset key as set forth in claim 16 wherein the reset member comprises at least one rib formed on an inner wall of the shroud.

18. A reset key as set forth in claim 17 wherein there is a plurality of ribs located at circumferentially spaced locations around the inner wall of the shroud.

19. A reset key as set forth in claim 15 further comprising a shaft mounted on the tubular shroud, the shaft being adapted to be received in a central axial passageway of the needle.

20. A reset key as set forth in claim 19 wherein the shaft is generally coaxial with the tubular shroud.

\* \* \* \* \*